(12) United States Patent
Money

(10) Patent No.: US 6,301,505 B1
(45) Date of Patent: Oct. 9, 2001

(54) STIMULUS OUTPUT MONITOR AND CONTROL CIRCUIT FOR ELECTRICAL TISSUE STIMULATOR

(75) Inventor: David Kerry Money, Pennant Hills (AU)

(73) Assignee: Cochlear Limited, New South Wales (AU)

(*) Notice: Subject to any disclaimer, the term of this patent is extended or adjusted under 35 U.S.C. 154(b) by 0 days.

(21) Appl. No.: 09/454,028

(22) Filed: Dec. 3, 1999

(30) Foreign Application Priority Data

Jun. 11, 1999 (WO) .................................. PCT/AU99/00470

(51) Int. Cl.[7] ....................................................... A61N 1/08
(52) U.S. Cl. ................................................. 607/63; 607/57
(58) Field of Search ................................. 607/63, 28, 55, 607/56, 57

(56) References Cited

U.S. PATENT DOCUMENTS 5,609,611   3/1997   Bolz et al. .
5,674,264 * 10/1997   Carter et al. ........................... 607/57

FOREIGN PATENT DOCUMENTS

A-32492/84   9/1983   (AU) .

OTHER PUBLICATIONS

WO 97/21324; International Publ. Date Jun. 12, 1997; International Appln. No. PCT/U95/00805; International Filing Date Dec. 1, 1995; Inventor: Carter, Paul Michael et al; Title: A Feedback System to Control Electrode Voltages in a Cochlear Stimulator and the Like.

* cited by examiner

*Primary Examiner*—Scott M. Getzow
(74) *Attorney, Agent, or Firm*—Gottieb, Rackman & Reisman, P.C.

(57) ABSTRACT

There is described an electrical tissue stimulating device, such as a cochlear prosthesis, which includes circuitry (47) for monitoring the build-up of undesirable residual voltages between stimulation electrodes. In the event that such a condition is sensed then an overvoltage signal is generated and transmitted to a switch controller (48). In response the switch controller controls electrode switches (42) in order to suppress stimulation of the monitored electrode(s) until the undesirable residual voltage has fallen to an acceptable level. As a result the build-up of undesirable inter-electrode voltages is reduced.

28 Claims, 5 Drawing Sheets

STIMULUS OUTPUT MONITOR AND CONTROL CIRCUIT FOR ELECTRICAL TISSUE STIMULATOR

FIELD OF THE INVENTION

This invention pertains to an electrical tissue stimulating device incorporating a safety control circuit. Such devices include cochlear implant prostheses, brain stem implants and functional electrical stimulators used for stimulating muscle tissue. In particular the present invention relates to a circuit which monitors voltage levels on tissue stimulating electrodes and takes action to reduce the presence of potentially dangerous voltage levels.

DESCRIPTION OF THE PRIOR ART

A problem with prior art electrical tissue stimulator systems is that a residual voltage may build up between stimulation electrodes and tissue due to charge imbalance in the applied stimulation pulses. Such residual voltages can lead to undesirable phenomenon occurring such as electrolytic reactions between tissue and electrodes.

Several schemes have been proposed in the past for dealing with this problem in the context of cochlear implant prostheses. For example, one standard scheme, used in a cochlear prosthesis and described in commonly owned U.S. Pat. No. 4,408,608 involves shorting the electrodes subsequent to the application of a stimulation pulse. The shorting step dissipates charge build up and so reduces the residual electrode voltage.

More recently in U.S. Pat. No. 5,674,264 also owned by the present applicant, there is described a scheme in which electrode voltages are monitored. In the event that a residual voltage is detected then the shape of the next biphasic stimulation pulse is modulated in order to reduce that residual voltage. The modulation involves altering the amplitude or duration of one of the phases of subsequent stimulations in order to drive the residual voltage towards zero.

Both of the above described solutions to the problem of reducing residual electrode voltages have their limitations.

While electrode shorting is highly effective at present, there is a trend in tissue stimulator design towards higher stimulation rates. At higher stimulation rates the time available for shorting is reduced and may be insufficient to permit the residual voltage to fall to a desirably low level. With respect to the second approach there are limitations as to the degree of compensation which may be effected by modulating a single biphasic stimulation pulse so that several stimulation cycles may be required before the residual voltage falls to a desirably low level. A further problem with the system of U.S. Pat. No. 5,674,264 is that it is reasonably complex to implement which is in conflict with design aims for miniaturisation, cost effectiveness, reliability and simplicity.

OBJECTIVES AND SUMMARY OF THE INVENTION

In view of the above limitations of the prior art it is an objective of the present invention to provide a tissue stimulating device including a means for reducing potentially unsafe residual electrode voltage levels.

According to the present invention there is provided an electrical tissue stimulator including:

a) overvoltage monitoring means arranged to monitor at least one electrode of a plurality of electrodes subsequent to delivery of an electrical stimulation signal by said at least one electrode and to generate a suitability-for-stimulation indication or an overvoltage indication in respect of said at least one electrode; and b) stimulation means coupled to said plurality of electrodes and arranged to apply said stimulation signals, said stimulation means being responsive to said overvoltage monitoring means, said stimulation means applying a stimulation by means of said at least one electrode only in the presence of a corresponding suitability-for-stimulation indication.

Preferably said stimulation means comprises a first portion arranged to generate stimulation commands specifying said stimulation signals and a second portion responsive to said first portion and arranged to generate said stimulation signals in accordance with said commands, said second portion being further responsive to said overvoltage monitoring means whereby said second portion generates a stimulation signal for delivery by a first electrode in accordance with a stimulation command only in the presence of a suitability-for-stimulation indication corresponding to said electrode.

Said electrical tissue stimulator may be arranged as a cochlear implant prosthesis.

Alternatively in the presence of a command to stimulate by means of said first electrode and in the presence of an overvoltage indication, said second portion is arranged to short-circuit said first electrode.

Preferably in the presence of a command to stimulate by means of a first electrode and in the presence of an overvoltage indication in respect of said first electrode said second portion is arranged to open-circuit said first electrode. Open-circuiting is preferable in the case of tissue stimulators which make use of capacitor-coupled stimulation electrodes.

Preferably said overvoltage monitoring means is arranged to measure a voltage difference between a first intra-cochlear electrode and an extra-cochlear electrode and on the basis of said voltage difference generate either said overvoltage indication or said suitability-for-stimulation indication.

In a further embodiment said overvoltage monitoring means is arranged to measure a voltage difference between a first intra-cochlear electrode and a second intra-cochlear electrode and on the basis of said voltage difference generate either said overvoltage indication or said suitability-for-stimulation indication.

Alternatively said overvoltage monitoring means may be arranged to measure a voltage difference between a first subset of electrodes and a second subset of electrodes and on the basis of said voltage difference generate either said overvoltage indication or said suitability-for-stimulation indication in respect of each electrode of said first subset.

Preferably said overvoltage monitoring means detects the presence of overvoltage conditions 1 to 50 micro-seconds prior to the time for commencement of a stimulation specified by a stimulation command.

In one embodiment said overvoltage monitoring means includes multiplexing means arranged to selectively couple electrodes of said plurality of electrodes to a comparator means; said comparator means arranged to generate a suitability-for-stimulation indication if a voltage associated with a selectively coupled electrode falls within a predetermined range and to generate an overvoltage indication if said voltage falls outside said range.

DETAILED DESCRIPTION OF THE INVENTION

While the present invention is applicable to controlling unwanted residual voltages on the electrodes of electrical tissue stimulators in general, it will be explained in the context of a cochlear implant prosthesis.

Figure 1:
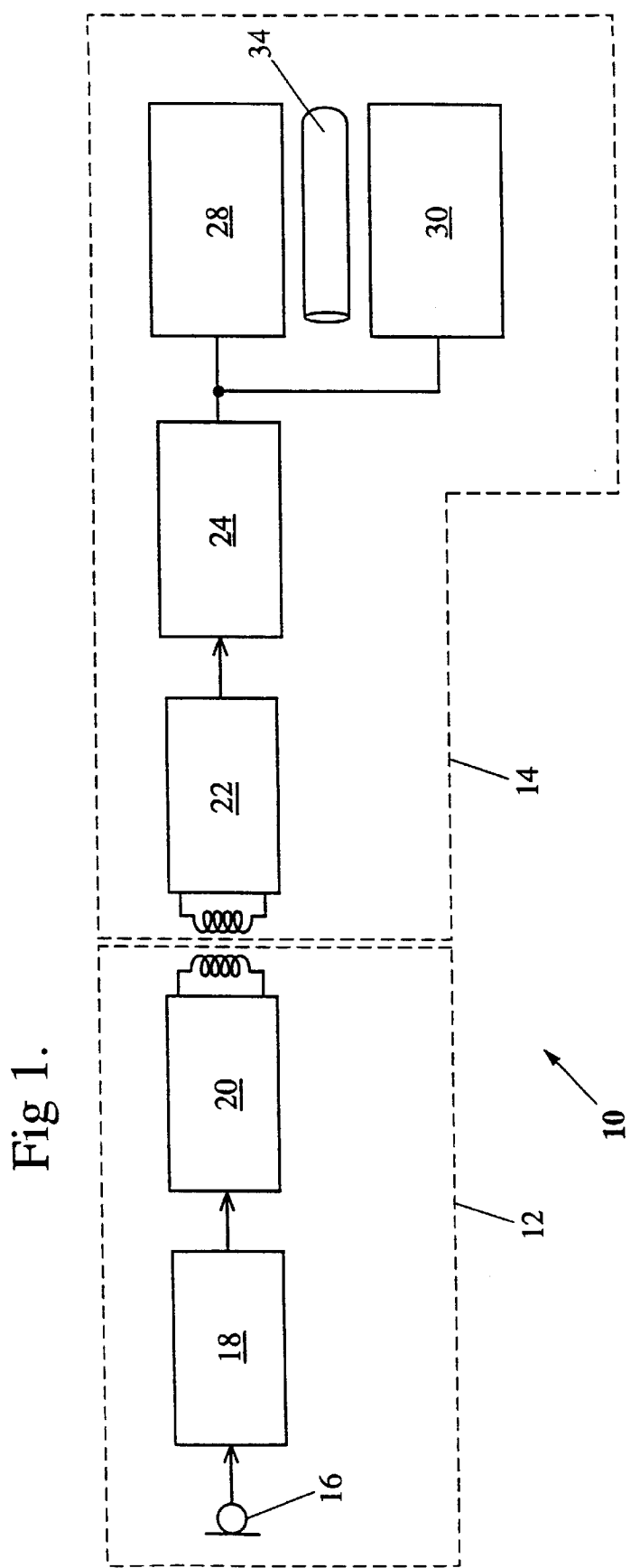
FIG. 1 shows a schematic diagram of a cochlear implant system.

Referring firstly to FIG. 1, a cochlear implant system 10 constructed in accordance with this invention includes an external component 12 and an implantable or internal component 14. External component 12 uses a microphone 16 for sensing ambient sounds and generating corresponding electrical signals. These signals are sent to a signal processor 18 which processes the signals and generates corresponding encoded signals. The encoded signals are provided to a transmitter 20 for transmission to the implantable component 14 by means of a pair of inductively coupled transcutaneous coils 13.

Figure 2:
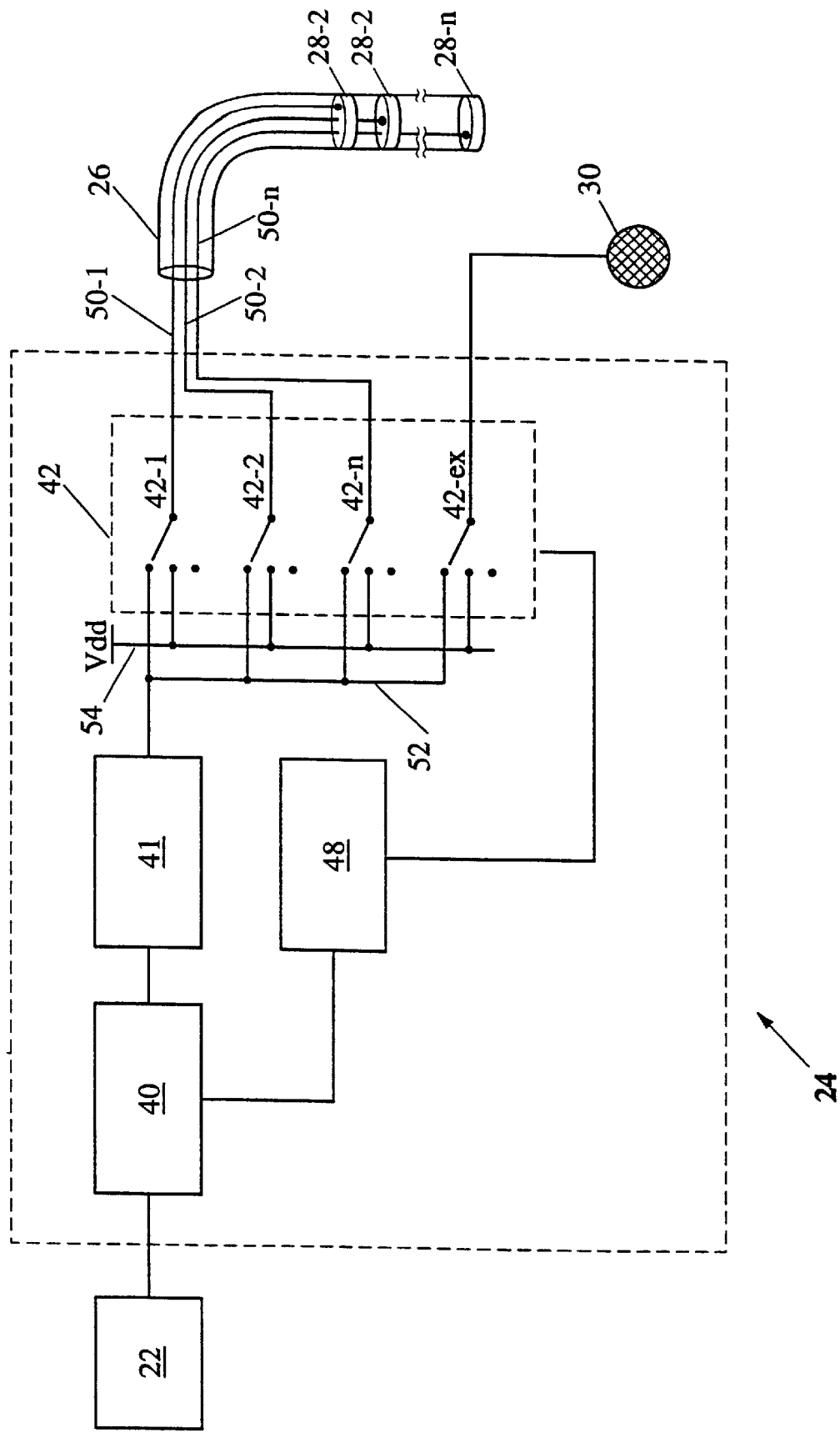
FIG. 2 shows a more detailed schematic diagram of a portion of the system depicted in FIG. 1.

Referring now to FIG. 2, the decoder stimulator 24 includes a decoder 40, current sink 41, switch controller 48, a plurality of switches 42-1, 42-2, . . . , 42-n, collectively referred to as switches 42. Each of the switches 42 is connected to corresponding leads 50-1, 50-2, . . . , 50-n, collectively referred to as leads 50 which are bundled together to form cable 26. One or more extra cochlear electrodes 30 may also be connected to some of the switches 42.

The circuit shown in FIG. 2 can perform a number of different functions. Its normal sequence of operation is as follows. Initially, before any stimulation signals are applied the leads 50 are shorted together by switches 42. For this purpose, each of the switches 42 is a single pole three position switch. The switches 42 can be selectively coupled to signal bus 52 or to shorting bus 54. The shorting bus is connected to a reference voltage capable of sourcing current, such as Vdd. The default state for the system is to have all leads 50 shorted together. This is achieved when all the switches 42 are thrown into the second position by switch controller 48. In this position, charge accumulated on the electrodes of electrode array 28 is dissipated so that the residual voltage difference between the electrodes prior to the application of stimulation is close to zero. Prior to the next stimulation the electrodes are disconnected from the shorting bus by setting all the switches 42 to the third (open-circuit) position, in readiness for stimulation.

Decoder/stimulator 24 produces a bipolar pulse as follows. Under control of decoder 40, current sink 41 produces a current pulse of specified amplitude and duration. To generate the first phase of the output pulse, one of the switches 42 is connected to signal bus 52. A second of the switches 42 is connected to the shorting bus. All other switches 41 are set open circuit. The current pulse from the current sink is thus directed between the two electrodes selected by switches 42. An inter-phase gap (a brief pause between the first and second pulses which make up the biphasic stimulation waveform) is generated by briefly setting all of the switches 42 to the open position. To generate the second phase, the switch 42 which connected an electrode to the signal bus is thrown to connect the same electrode to shorting bus 54. At the same time the switch which connected an electrode to shorting bus 54 is thrown to connect the same electrode to signal bus 52. Current sink 41 then generates a second pulse of equal amplitude and duration to the first pulse, which is applied through the two selected electrodes in the reverse direction to the first pulse. Thus a biphasic pulse is produced between the two electrodes which stimulates cochlear nervous tissue 34 of FIG. 1. The two phases of the current pulse are both produced by the same current sink, and so are very closely matched, resulting in a minimum of residual charge on the electrodes. Once the two phases of the pulse have been delivered, all of the switches 42 are returned to the resting position, connected to shorting bus 54 in order to reduce any residual charge remaining on the electrodes.

A monopolar extracochlear pulse is generated in the same manner as described above, but one of the two selected electrodes is an extracochlear electrode.

A common ground pulse is produced by connecting all but one switch firstly to the shorting bus, with the exceptional switch connected to the signal bus. The switch positions are then reversed to deliver the second phase of the biphasic pulse.

Figure 3:
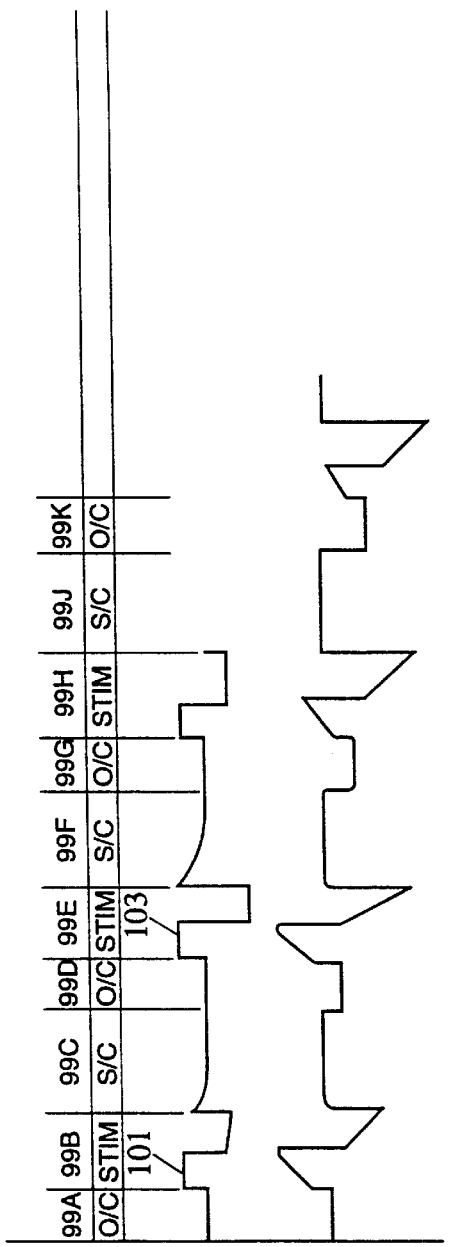
FIG. 3 shows typical waveforms associated with a single stimulated electrode with respect to a second or indifferent electrode in use in a prior art electrical tissue stimulator.

Referring now to FIG. 3 the waveforms associated with a single intracochlear electrode during a typical period of operation of a cochlear prosthesis are depicted. In the interests of clarity the interphase gap alluded to earlier has not been shown. After initial open circuiting of the electrode during period 99A a stimulation period 99B is entered in which biphasic current waveform 101 is applied by means of two sets of electrodes. Typically the two sets of electrodes would be just two electrodes—one electrode on the electrode array and one extracochlear electrode (a monopolar mode stimulation) or two electrodes on the electrode array (a bipolar mode stimulation). Alternatively, the first set of electrodes consists of one electrode on the electrode array, and the second set of electrodes consists of all the remaining electrodes on the electrode array shorted together (a common ground mode stimulation). Other groupings of eletrodes are also possible. The following description will address stimulation applied to a pair of electrodes, but it will be understood that each of the electrodes in the pair could comprise a set of electrodes, for example a number of electrodes 28-1, . . . , 28-n as shown in FIG. 2, short circuited together.

After the stimulation pulse has been delivered, a short-circuit period 99C is entered in which all of the electrodes are shorted together so as to reduce any residual charge. Finally, just before the next stimulus is to be delivered a new open-circuit period 99D is commenced.

During the open-circuit period 99D a voltage difference Vp is measured between the two sets of electrodes. An "overvoltage condition" is said to exist when Vp falls outside the range +Vt to −Vt. Typically Vt will be about 250 mV.

Whether or not the voltage difference measured between the two sets of electrodes during the open-circuit period is close to zero depends on several factors. Two critical ones are whether or not the charge associated with the first phase of stimulation pulse 101 is equal to that in the second phase, and whether or not the short-circuit period 99C is sufficiently long. In the present example Vp is slightly more negative during open-circuit period 99D than during the preceding open-circuit period 99A, but remains in the desired range of +Vt to −Vt. During period 99E current stimulation 103 is applied. It will be noted that applied pulse 103 is substantially assymetrical and as a consequence the following shorting period 99F is insufficient to remove all of the residual charge. Therefore, Vp falls outside the desired range when measured during the next open-circuit period 99G. Furthermore, subsequent stimulus pulse during period 99H, in the example shown, does not remove the residual charge, and so Vp continues to take an undesirable level when measured in the next open-circuit period 99K.

Figure 4A:
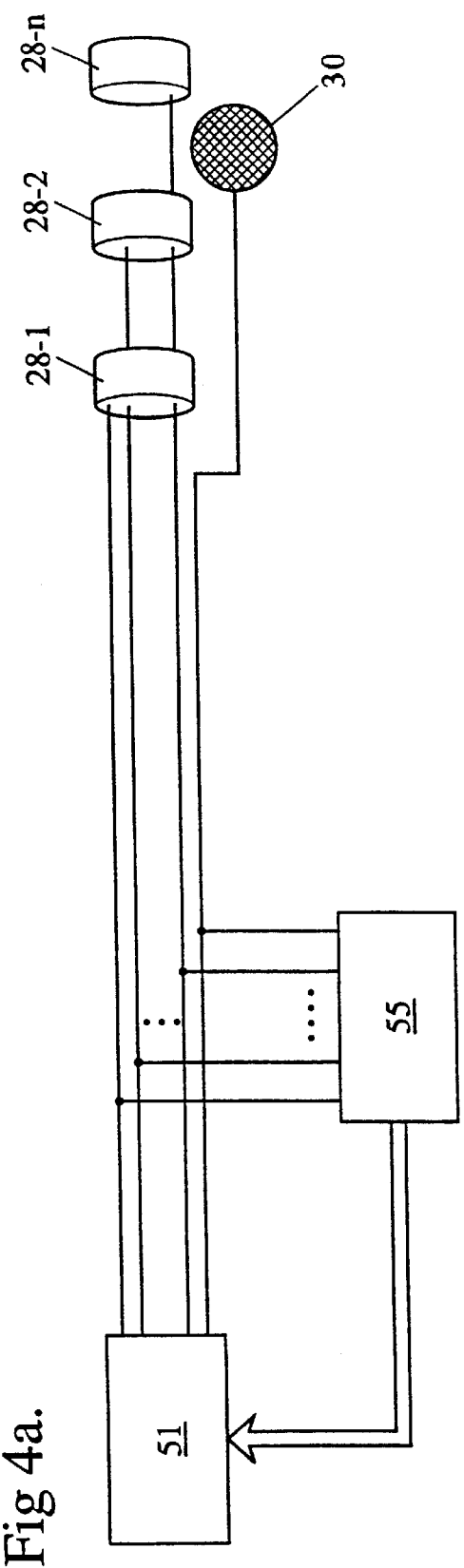
FIG. 4A shows a tissue stimulating system according to the present invention.

Referring now to FIG. 4A there is shown a high level diagram of a tissue stimulating device according to the present invention. The diagram of FIG. 4A includes a stimulation means 51 which includes circuitry for determining the parameters of the stimulations to be applied by intra-cochlear electrodes 28 and extra-cochlear electrode(s) 30. For example typically parameters such as the amplitude and width of the biphasic stimulation pulse to be delivered and also the particular electrode of the array and the mode (bipolar, monopolar, common ground etc) of the stimulation will need to be determined. In the context of a cochlear prosthesis the determination of these parameters will be made with reference to a sound processing and stimulation strategy. Other strategies are used in other types of tissue stimulators, for example a tissue stimulator used to alleviate seizures would make use of a different stimulation strategy. Whatever the strategy used and the parameters for stimulation determined, stimulation means 51 also includes circuitry for generating electrical stimulations in accordance with the determined parameters. Importantly, according to the invention overvoltage monitor 55 is coupled to electrodes 28, 30 and after the delivery of a stimulation, and prior to the next stimulus, produces an indication as to whether the residual voltage on each electrode is outside or inside a predetermined range. Stimulation means 51 is responsive to the indications provided by the overvoltage monitor prior to delivering stimulations and will only apply stimulation to a particular electrode if the overvoltage monitor indicates that it is appropriate to do so. Alternatively, it would be possible to measure the threshold voltage on individual electrodes with reference to an independent electrode.

Figure 4B:
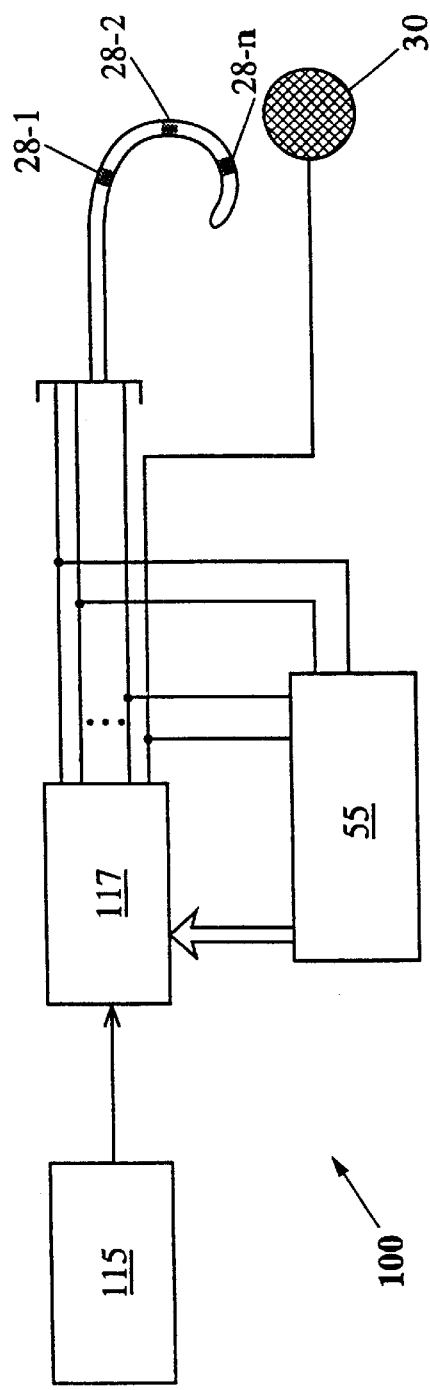
FIG. 4B shows the tissue stimulating system of FIG. 4A incorporating a partitioning of the command and stimulation module.

Referring now to FIG. 4B there is shown a more detailed diagram of the device of FIG. 4A. In FIG. 4B the stimulation means of FIG. 4A has been divided into two portions, a first portion, being stimulation command generator 115, arranged to generate stimulation commands specifying the parameters of stimulation signals to be delivered and a second portion, stimulation generator 117, arranged to generate the stimulation signals in response to commands from command generator 115. In the context of a cochlear prosthesis, stimulation command generator 115 comprises microphone 16 signal processor 18, transmitter 20, receiver 22 and decoder 40 as shown in FIGS. 1 and 2.

Stimulation generator 117 receives commands from stimulation command module 115 and, on the basis of those commands, delivers electrical stimulation signals by means of electrodes 28-1, . . . , 28-n and extracochlear electrode 30. Once again, in the context of a cochlear prosthesis, stimulation generator 117 comprises switch controller 48, programmable current sink 41 and switch array 42.

Finally, tissue stimulation device 100 includes an overvoltage monitor 55 which is connected in order that it may monitor the voltages difference between subsets of electrodes 28-1, . . . , 28-n, 30 subsequent to the delivery of each stimulation pulse. For example, in the event that overvoltage monitor 55 detects an electrode voltage difference between electrode 28-2 and electrode 30, of magnitude greater than preset threshold value Vt then an overvoltage condition is indicated in an internal register. The overvoltage indication is changed to a "suitability-to-stimulate" indication only when the residual voltage between electrode 28-2 and electrode 30 is next found to be within the predetermined range. When a subsequent command to stimulate via electrode 28-2 is received by stimulation means 117 from stimulation command generator 115 then that command is only carried out by stimulation means 117 in the event that overvoltage monitor 55 indicates a suitability-to-stimulate condition in respect of electrode 28-2. It will be understood that a suitability-to-stimulate condition might simply be indicated by the absence of an overvoltage indication, or vice versa.

It will be noted that in FIG. 4B the output of the overvoltage monitor is shown to be coupled to the stimulation means 117. Other arrangements are possible however, for example the output of overvoltage monitor 55 could be coupled to stimulation command generator 115 in which case commands to stimulate via a particular electrode would only be generated in the event that the overvoltage monitor indicated an appropriateness to do so. The effectiveness of the arrangement of FIG. 4B in reducing undesirable residual electrode voltages will now be explained with reference to FIG. 5.

Figure 5:
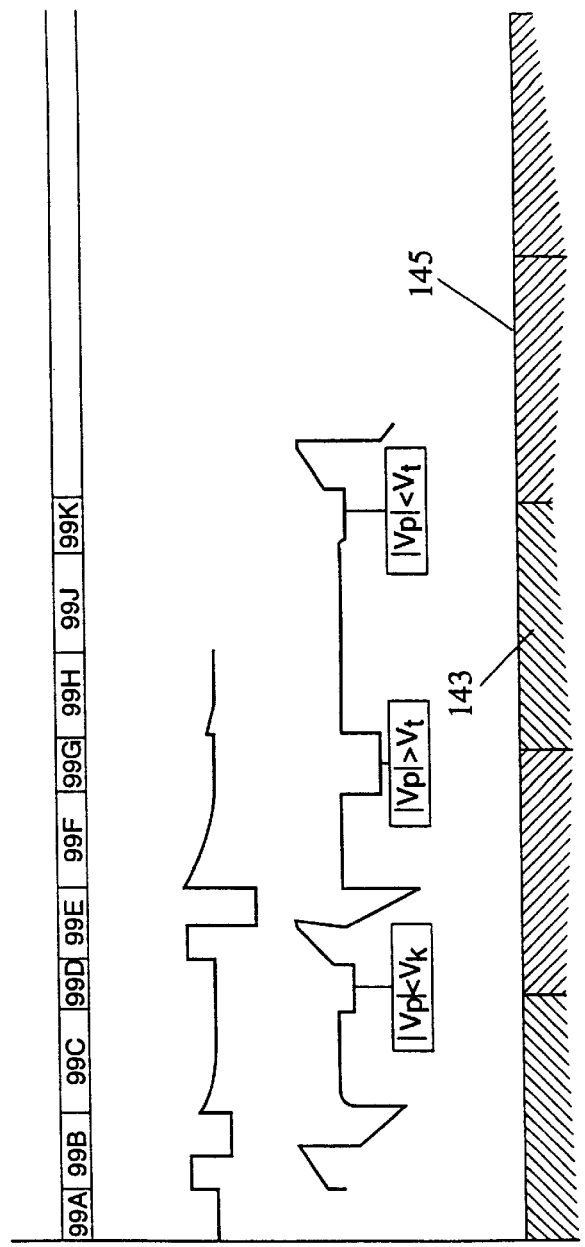
FIG. 5 shows typical waveforms associated with a single stimulated electrode with respect to a second, indifferent electrode in use in an electrical tissue stimulator according to the present invention.

Referring now to FIG. 5 it will be noted that the residual voltage on electrode 28-2 measured relative to extracochlear electrode 30, is monitored in the open-circuit period between a short-circuit period and a stimulation period. When measured during the open-circuit period 99G (the magnitude of Vp is found to be greater than Vt). Consequently an overvoltage indication 143 is made in respect of electrode 28-2.

Subsequently although a command is received to stimulate in period 99H that command is not carried out by stimulation means 117. Preferably during period 99H the switches are left in the short circuit position. The magnitude of Vp is next measured during the following open circuit period 99K at which point it has fallen within the range +Vt to −Vt so that overvoltage indication 143 is replaced with suitability-to-stimulate indication 145. As a result the next command to stimulate via electrode 28-2 will be carried out by stimulation means 117 rather than being suppressed.

Figure 6:
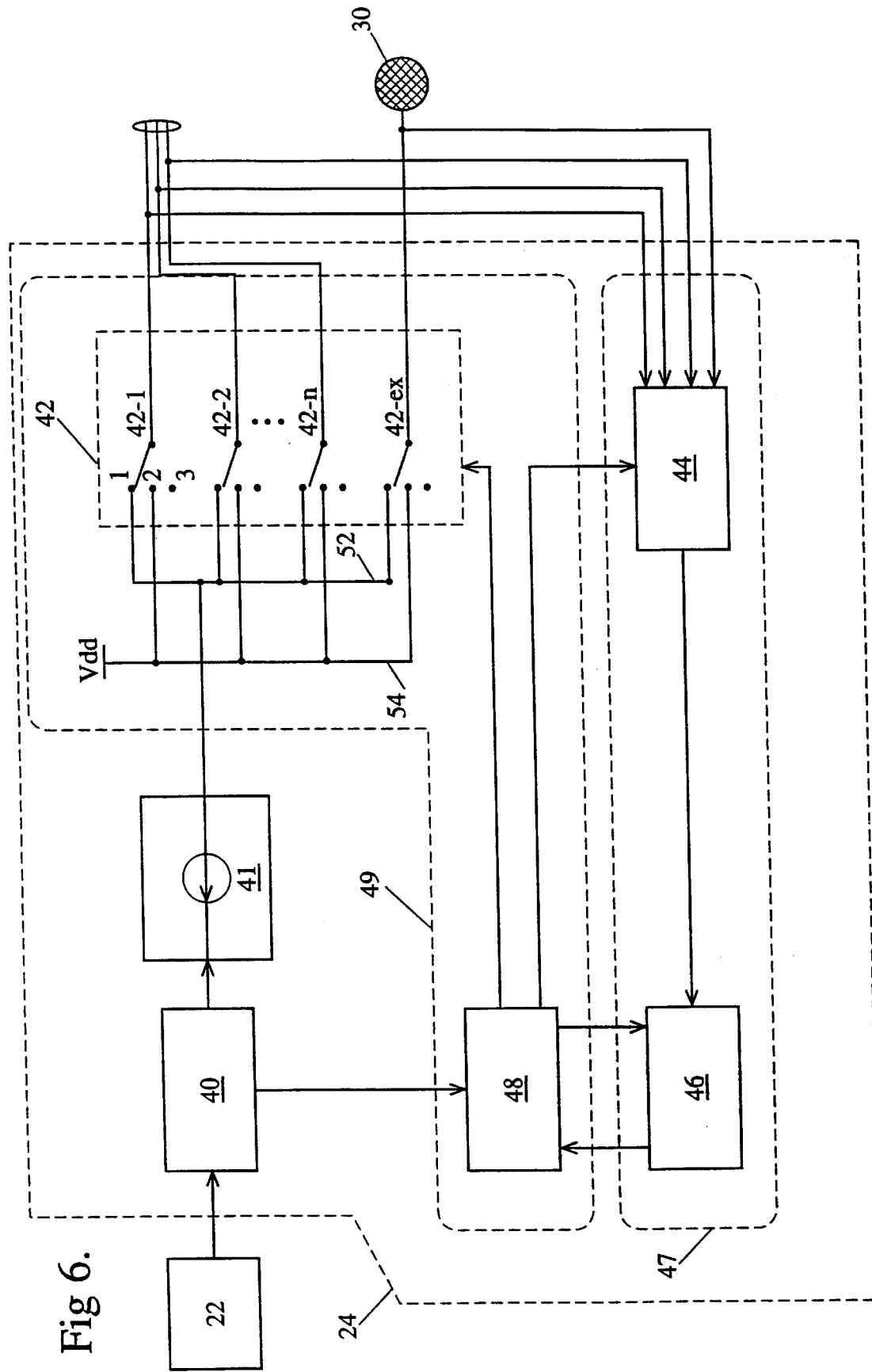
FIG. 6 shows an implementation of the overvoltage monitor of FIG. 4.

Referring now to FIG. 6 a further embodiment of the invention is depicted. It will be noted that multiplexer 44 is coupled at one side to each of the electrode leads 50 and 30. The other side of multiplexer 44 is connected to voltage monitor 46. Under control of switch controller 48 the multiplexer sequentially connects each pair of electrodes to voltage monitor 46 preferably during an open circuit period. The voltage monitor determines whether or not the voltage being monitored falls within a predetermined range. If it does not fall within the range then a signal is sent to switch controller 48 which indicates the overvoltage condition in respect of the electrodes whose voltage is being monitored. Upon a command to stimulate being generated by decoder 40 switch controller 48 firstly checks the presence of a suitability-to-stimulate indication in respect of the electrodes that are to deliver the stimulation pulse. However if an overvoltage indication exists in respect of the electrode in question then switch controller 48 does not set the corresponding switch 42 to the first position in order to carry out the stimulation command but rather sets it to the second position thereby short circuiting the electrode and suppressing the stimulation command.

Preferably the residual electrode voltage measurement should occur close enough to commencement of stimulation so that the determined residual electrode voltage reflects the state of the respective electrode accurately but with enough time left to allow the switch controller 48 to take action if necessary. Alternatively, the voltage can be measured immediately after the stimulation pulse, or at any other time between pulses, while open circuiting the electrodes.

As discussed above, the voltage measured by monitor 46 is associated with the charge built up on particular electrodes. This charge may be determined by using other types of sensors as well, such as for example a current sensor.

Obviously, numerous modifications can be made to the invention without departing from its scope as defined in the appended claims.

The claims defining the invention are as follows:

1. An electrical tissue stimulator including:
    a) overvoltage monitoring means arranged to monitor at least one electrode of a plurality of electrodes subsequent to delivery of an electrical stimulation signal by said at least one electrode and to generate a suitability-for-stimulation indication in respect of said at least one electrode; and
    b) stimulation means coupled to at least one of a plurality of electrodes and arranged to apply said stimulation signals, said stimulation means being responsive to said overvoltage monitoring means, said stimulation means applying a stimulation by means of said at least one electrode during a predetermined pulse period only in the presence of a corresponding suitability-for-stimulation indication.

2. An electrical tissue stimulator according to claim 1, wherein said stimulation means comprises a first portion arranged to generate stimulation commands specifying said stimulation signals and a second portion responsive to said first portion and arranged to generate said stimulation signals in accordance with said commands, said second portion being further responsive to said overvoltage monitoring means whereby said second portion generates a stimulation signal for delivery by a first electrode in accordance with a stimulation command only in the presence of a suitability-for-stimulation indication corresponding to said electrode.

3. An electrical tissue stimulator according to claim 1 or claim 2 further arranged as a cochlear implant prosthesis.

4. An electrical tissue stimulator according to claim 3, wherein in the presence of a command to stimulate by means of said first electrode and in the presence of an overvoltage indication in respect of said first electrode said second portion is arranged to open-circuit said first electrode.

5. An electrical tissue stimulator according to claim 3, wherein in the presence of a command to stimulate by means of said first electrode and in the presence of an overvoltage indication, said second portion is arranged to short-circuit said first electrode.

6. An electrical tissue stimulator according to claim 3, wherein said overvoltage monitoring means is arranged to measure a voltage difference between a first intra-cochlear electrode and an extra-cochlear electrode and on the basis of said voltage difference generate either said overvoltage indication or said suitability-for-stimulation indication.

7. An electrical tissue stimulator according to claim 3, wherein said overvoltage monitoring means is arranged to measure a voltage difference between a first intra-cochlear electrode and a second intra-cochlear electrode and on the basis of said voltage difference generate either said overvoltage indication or said suitability-for-stimulation indication.

8. An electrical tissue stimulator according to claim 3, wherein said overvoltage monitoring means is arranged to measure a voltage difference between a first subset of electrodes and a second subset of electrodes and on the basis of said voltage difference generate either said overvoltage indication or said suitability-for-stimulation indication in respect of each electrode of said first subset.

9. An electrical tissue stimulator according to claim 3, wherein said overvoltage monitoring means detects the presence of overvoltage conditions 1 to 50 micro-seconds prior to the time for commencement of a stimulation specified by a stimulation command.

10. An electrical tissue stimulator according to claim 3, wherein said overvoltage monitoring means includes multiplexing means arranged to selectively couple electrodes of said plurality of electrodes to a comparator means; said comparator means arranged to generate a suitability-for-stimulation indication if a voltage associated with a selectively coupled electrode falls within a predetermined range and to generate an overvoltage indication if said voltage falls outside said range.

11. The electrical stimulator of claim 1 wherein said suitability-for-stimulation indication is generated when the voltage on said one electrode is within a predetermined range.

12. A cochlear implant system for providing stimulation signals directly to a patient's aural nerve corresponding to ambient sounds comprising:
    a processor that generates stimulation signals at predetermined pulse periods, said stimulation signals corresponding to said ambient sounds;
    a plurality of electrodes for applying said stimulation signals to the patient's aural nerve during said predetermined pulse periods;
    a switching mechanism for selective switching of said stimulation signals to said electrodes; and
    a sensor for sensing a preselected parameter on said electrodes indicative of an excessive charge, said switching mechanism being coupled to said sensor to switch said stimulation signals to said electrodes only during pulse periods during which said preselected parameter does not indicate said excessive charge.

13. The system of claim 12 wherein said sensor is a voltage monitor.

14. The system of claim 12 further wherein said plurality of electrodes includes an intracochlear and an extracochlear electrode and wherein said sensor measures an instantaneous voltage between said intracochlear and said extracochlear electrode.

15. The system of claim 12 wherein said sensor measures a voltage between two electrodes.

16. The system of claim 12 further comprising an external and an internal component, said processor being disposed in said external component and said switching mechanism being disposed in said internal component.

17. A cochlear implant system comprising:
    an external component receiving ambient sounds, said external component including a processor for converting said sounds into encoded signals and a transmitter for transmitting said encoded signals; and
    an internal component including a receiver for receiving said encoded signals, a decoder for decoding said decoded signals into stimulation signals, a plurality of electrodes for applying said stimulation signals to a patient's aural nerve, a switching mechanism for switching said stimulation signals to said electrodes, and a sensor for sensing a preselected parameter on said electrodes indicative of an excessive charge, said sensor changing an operation of said sensor to prevent the delivery of the stimulation signals during a predetermined period if said sensor senses said predetermined parameter.

18. The system of claim 17 wherein said switching mechanism suppresses said second stimulation signal in the presence of said abnormal parameter.

19. The system of claim 17 further comprising a shorting circuit for selectively shorting one electrode if said abnormal parameter is present.

20. The system of claim 17 comprising intracochlear and extracochlear electrodes.

21. The system of claim 20 wherein said one electrode is an intracochlear electrode.

22. The system of claim 21 wherein said one electrode is shorted to another intracochlear electrode.

23. The system of claim 21 wherein said one electrode is shorted by said shorting circuit to an extracochlear electrode.

24. A method of applying electrical stimulation to body tissues over a set of electrodes comprising the steps of:

measuring the voltage on the electrodes of said set; and applying during a subsequent period a stimulation pulse to said set of electrodes only if the voltage is within a preselected range.

25. The method of claim 24 wherein said stimulation pulse is a monophasic pulse.

26. The method of claim 24 wherein said stimulation pulse is a biphasic pulse.

27. The method of claim 24 further comprising shorting said electrodes prior to said step of measuring the voltage.

28. The method of claim 27 further comprising open-circuiting said electrodes, the voltage being measured while said electrodes are open circuited.

* * * * *